United States Patent [19]

Hutchings et al.

[11] 3,933,681

[45] Jan. 20, 1976

[54] ACTIVATION OF COPPER SALT PHENOL OXIDATION CATALYSTS

[75] Inventors: David A. Hutchings, Stow; Michael F. Farona, Cuyahoga Falls, both of Ohio

[73] Assignee: The Goodyear Tire & Rubber Company, Akron, Ohio

[22] Filed: Mar. 13, 1974

[21] Appl. No.: 450,946

[52] U.S. Cl............... 252/413; 252/415; 260/396 R
[51] Int. Cl.² ................... B01J 27/32; B01J 27/28; C07C 49/62
[58] Field of Search.......... 252/413, 415; 260/396 R

[56] References Cited
UNITED STATES PATENTS
3,796,732   3/1974   Brenner ................... 260/396 R FOREIGN PATENTS OR APPLICATIONS
45-24767   8/1971   Japan .............................. 260/396 R Primary Examiner—Winston A. Douglas
Assistant Examiner—P. E. Konopka
Attorney, Agent, or Firm—F. W. Brunner; C. R. Schupbach; J. Y. Clowney

[57] ABSTRACT

A method of activating inactive copper salt catalysts for phenol oxidation by the addition of acid.

3 Claims, No Drawings

ACTIVATION OF COPPER SALT PHENOL OXIDATION CATALYSTS

The present invention relates to a method of activating copper salt catalysts for phenol oxidation which have been deactivated through the formation of insoluble complexes.

Copper salts are used to catalyze oxidation of phenols to benzoquinones. In this process a portion of the copper catalyst forms an insoluble precipitate which lacks catalytic activity. It is thought that solvents and products from the process react with the copper salt catalysts to form this inactive complex. This necessitates discarding at least the precipitated portion of the catalyst, and requires the addition of fresh catalyst, because carrying out the process in the presence of the inactive complex results in a decrease in yield and purity of benzoquinone.

It is therefore desirable to be able to reactivate the copper catalyst and allow it to be reused.

It has now been discovered that an inactive copper salt complex can be transformed to an active form by treating the complex with acids. Addition of acid dissolves the precipitate and regenerates the copper catalyst.

Representative examples of acids useful in the practice of the present invention are sulfuric, hydrochloric, nitric, trifluoroacetic, phosphoric, perchloric and toluene sulfonic. Mixtures of acids can be used.

Representative examples of complexes which can be regenerated using the process of the present invention are complexes formed from cuprous or cupric salts used as catalysts such as copper chlorides, copper bromides, copper iodides, copper fluorides, copper cyanate, copper cyanide, and copper thiocyanate.

The process of this invention can be carried out at room temperature and atmospheric pressure. Temperatures from 20° C. to 120° C. are preferred with temperatures from 25° C. to 110° C. being most preferred. Temperatures higher than 120° C. can be used if desired. Pressures higher or lower than atmospheric pressure can be used.

The amount of acid required to dissolve the complex and reactivate the catalyst can vary widely. From about .001 mole to 1.0 mole of acid per gram of inactive complex can be used. From about .005 mole to .1 mole of acid per gram of inactive complex is preferred.

The practice of the invention is illustrated in the examples given below in which parts and percentages are by weight unless otherwise indicated. Example 1 is a comparative example illustrating the phenol oxidation producing the inactive catalyst precipitate. Examples 2, 3, 4 and 5 show various acids used to destroy the complex and activate the catalyst. Example 6 shows the activated catalyst produced in Example 2 being used for phenol oxidation. Examples 7 and 8, when compared, show the effect of excess acid on the oxidation of phenol to benzoquinone.

EXAMPLE 1

Thirty milliliters of methanol, 2 grams of phenol and one gram of copper (II) chloride catalyst were charged into a 75 cubic centimeter reaction bomb. The bomb was sealed and pressurized to 500 pounds per square inch gauge (PSIG) oxygen pressure and heated to 65° C. The contents were agitated. After 4 hours reaction time the bomb was depressurized and the contents sampled for phenol and benzoquinone. Approximately 50 percent of the catalyst was in the form of an insoluble precipitate. A portion of this insoluble precipitate was tested for activity as a phenol oxidation catalyst using micro-oxidation techniques and found to be completely inactive. During the reaction phenol was converted to benzoquinone as shown.

| Time (Minutes) | Percent Conversion |
|---|---|
| 30 | 34 |
| 60 | 46 |
| 90 | 58 |

EXAMPLE 2

Forty milligrams of the inactive copper complex obtained as described in Example 1, 100 milligrams of phenol and 1 gram of methanol were placed in a ½ ounce bottle. The copper complex was completely insoluble in the methanol. One microliter increments of concentrated hydrochloric acid (38% by weight aqueous) were added to the reaction mixture. The complex was in solution after 11 microliters of concentrated hydrochloric acid were added.

EXAMPLE 3

Twenty milligrams of the inactive complex obtained as described in Example 1, 100 milligrams of phenol and one cubic centimeter of methanol were added to a ½ ounce bottle. The complex was insoluble in the methanol. Two microliter portions of concentrated sulfuric acid were added until 10 microliters were in the bottle. The insoluble complex went into solution with the methanol and acid when the mixture was heated with steam at 100° C. An oxidation was run with the solution formed by charging 100 microliters of said solution into a micro reactor, heating to 65° C., and charging 500 pounds per square inch gauge oxygen pressure. After oxidizing for 60 minutes, 29.6 percent conversion of phenol to benzoquinone was obtained.

EXAMPLE 4

Twenty grams of the insoluble copper salt complex as described in Example 1, 100 milligrams of phenol and 1 gram of methanol were mixed in a ½ ounce bottle. Two microliter portions of trifluoroacetic acid were added until 10 microliters were in solution. Upon addition of the trifluoroacetic acid and heating with steam at 100° C. appeared to dissolve approximately one-half of the catalyst complex, 100 microliters of this solution was charged into a micro reactor and reacted under the same conditions as described in Example 2. After 60 minutes of oxidation, 2.47 percent conversion of the phenol to the benzoquinone was obtained. After 120 minutes reaction time, 4.19 percent phenol to benzoquinone conversion was obtained. The slower reaction rate was attributed to trifluoroacetic acid inhibition.

EXAMPLE 5

Twenty milligrams of the inactive copper salt complex obtained from Example 1, 100 milligrams of phenol and 1 gram of methanol were dissolved in a ½ ounce bottle. Twenty micrograms of toluene sulfonic acid were added and solution was effected under steam heat at 100° C. One-half of the insoluble complex appeared to go into solution. One hundred microliters of the solution were charged into a micro reactor and reacted under the same conditions as described in Example 2. Samples were taken at 30 and 60 minutes. After 30 minutes of oxidation, a conversion of less than 1 percent phenol to benzoquinone was obtained. After 60 minutes reaction time, 4.74 percent conversion of phenol to benzoquinone was obtained.

EXAMPLE 6

Two hundred microliters of the solution obtained from Example 2 were charged into a micro oxidation reactor. The reactor was charged to 500 pounds per square inch gauge oxygen pressure and heated to 65° C. The reactor was sampled at 30, 60 and 120 minutes using a microliter syringe and the contents analyzed utilizing gas chromatography.

| Time Minutes | Conversion Percentage | Benzoquinone Yield in Milligrams |
|---|---|---|
| 30 | 2.40 | 2.4 |
| 60 | 10.5 | 10.5 |
| 120 | 33.5 | 33.5 |

EXAMPLE 7

Twenty milligrams of the inactive catalyst obtained as described in Example 1 was added to 50 milligrams of phenol, .5 milliliters of methanol and 6 microliters of hydrochloric acid. The acid did not dissolve the inactive complex. The solution was heated to about 100° C. while 10 drops of additional methanol was added to compensate for evaporation. Approximately one-half of the inactive complex went into solution, said solution having a dark brown color. One hundred microliters were charged into a micro-oxidation reactor and oxidized at 65° C. under 500 pounds per square inch gauge (PSIG) oxygen. Samples were obtained and analyzed as described in Example 6 to determine phenol to benzoquinone conversion.

| Time (Minutes) | Percent Conversion |
|---|---|
| 30 | 12.2 |
| 60 | 26.0 |
| 90 | 35.4 |

EXAMPLE 8

This example was carried out in the same manner as Example 7 using 12 microliters of hydrochloric acid. Heating was again necessary. Approximately three-fourths of the complex dissolved to form a dark brown solution. Oxidation and sampling as described in Example 7 showed the following results:

| Time (Minutes) | Percent Conversion |
|---|---|
| 30 | 2.6 |
| 60 | 5.4 |
| 90 | 13.8 |

The results of the sample oxidation carried out with the reactivated copper salt catalyst clearly indicates that acid treatment is useful in regenerating the copper salt complex formed during phenol oxidation using methanol solvent.

Excess acid tends to inhibit the ability of the activated catalyst to oxidize phenol to benzoquinone. Different acids vary in their effect on the oxidation rate. Normally the acids are effective in the concentrations indicated herein.

The inactive copper salt complex can be activated by separating the benzoquinone from the reaction mixture and adding acid directly to said reaction mixture. A more preferred method is to separate the inactive complex from the reaction solution before adding acid.

While certain representative embodiments and details have been shown for the purpose of illustrating the invention, it will be apparent to those skilled in this art that various changes and modifications may be made therein without departing from the spirit or scope of the invention.

We claim:

1. A method of reactivating a deactivated phenol oxidation catalyst complex resulting from the oxidation of phenol in methanol solution to form benzoquinone, said oxidation catalyst selected from the group consisting of copper(I) or copper(II) salts of halogen ions, thiocyanate ions and cyanide ions comprising
    a. separating the inactive complex from the reaction solution
    b. mixing said inactive catalyst complex with phenol and methanol
    c. adding to said mixture from .001 mole to 1.0 mole per gram of inactive complex of at least one acid selected from the group consisting of sulfuric, hydrochloric, nitric, trifluoroacetic, phosphoric, perchloric and toluene sulfonic acid to the inactive catalyst and
    d. heating the resulting mixture until the complex dissolves.

2. A method as described in claim 1 above wherein the acid is selected from the group consisting of sulfuric and hydrochloric.

3. A method as described in claim 1 above wherein the halogen ions are selected from the group consisting of chlorine, bromine, and iodine.

* * * * *